United States Patent
Knighton et al.

(10) Patent No.: US 6,551,280 B1
(45) Date of Patent: Apr. 22, 2003

(54) THERAPEUTIC DEVICE AND SYSTEM

(75) Inventors: David R. Knighton, Minneapolis, MN (US); Vance D. Fiegel, New Brighton, MN (US)

(73) Assignee: Embro Corporation, St. Louis Park, MN (US)

( * ) Notice: Subject to any disclaimer, the term of this patent is extended or adjusted under 35 U.S.C. 154(b) by 79 days.

(21) Appl. No.: 09/607,719

(22) Filed: Jun. 30, 2000

(51) Int. Cl.⁷ .............................................. A61M 37/00
(52) U.S. Cl. ...................................... 604/133; 601/152
(58) Field of Search .................... 604/133, 9; 601/150, 601/152; 602/13, 3; 5/854, 713, 671

(56) References Cited

U.S. PATENT DOCUMENTS

| | | | |
|---|---|---|---|
| 3,600,727 A | * 8/1971 | Williams | ........................ 5/671 |
| 4,552,132 A | 11/1985 | Ruscigno | |
| 4,827,763 A | 5/1989 | Bourland et al. | |
| 4,947,500 A | * 8/1990 | Seller | ............................. 5/713 |
| 5,009,639 A | 4/1991 | Keymling | |
| 5,033,466 A | 7/1991 | Weymuller, Jr. | |
| 5,179,941 A | 1/1993 | Siemssen et al. | |
| 5,218,954 A | 6/1993 | van Bemmelen | |
| 5,411,509 A | 5/1995 | Hilal | |
| 5,527,293 A | 6/1996 | Zamierowski | |
| 5,556,169 A | 9/1996 | Parrish et al. | |
| 5,588,955 A | * 12/1996 | Johnson et al. | ............. 601/152 |
| 5,797,155 A | * 8/1998 | Maier et al. | .................... 5/654 |
| 5,865,772 A | * 2/1999 | George | .......................... 602/3 |
| 5,904,703 A | 5/1999 | Gilson | |
| 5,928,182 A | * 7/1999 | Kraus et al. | .................... 604/9 |
| 6,129,688 A | * 10/2000 | Arkans | ........................ 601/152 |
| 6,231,532 B1 | * 5/2001 | Watson et al. | .............. 601/150 |
| 6,315,745 B1 | * 11/2001 | Kloecker | ..................... 602/13 |

OTHER PUBLICATIONS

Chapter 1: "Physical Behaviour of Polymeric Foams—An Overview", Low Density Cellular Plastics: Physical Basis of Behaviour, Edited by N. C. Hilyard and A. Cunningham.

* cited by examiner

Primary Examiner—Teresa Walberg
Assistant Examiner—Leonid Fastovsky
(74) Attorney, Agent, or Firm—Popovich & Wiles, P.A.

(57) ABSTRACT

Therapeutic devices that provide support or pressure to tissue. Devices contain a material that is capable of being contracted from its relaxed state to an evacuated state. The material applies pressure to the tissue of a patient when the material is in its relaxed state. Reduction of pressure by application of a vacuum results in a contracted state of the device, so that the device can be applied or delivered to a patient. Release of vacuum results in a return to the relaxed state, thus providing a maximum desirable pressure to tissue and avoiding the possibility of over-pressure which can result in tissue damage or necrosis.

38 Claims, 9 Drawing Sheets

THERAPEUTIC DEVICE AND SYSTEM

FIELD OF THE INVENTION

The present invention relates to therapeutic devices and medical appliances that provide support or pressure to tissue. In particular, the invention relates to devices and appliances comprising open cell foam usefull in the treatment of diseases, disorders and injuries.

BACKGROUND OF THE INVENTION

Patients suffering from injury or disease or recovering from surgery may be treated by the application of constant or intermittent pressure. Pressure is used to control swelling, increase blood flow, and immobilize tissue.

In cases of acute injuries, such as acute joint injury, three treatments are employed simultaneously. First, the injured region is chilled (such as with ice); second, pressure is applied using an elastic bandage; and third, immobilization is achieved using a splint. For example, an athletic trainer applies elastic wrap to an injured ankle or knee and then immobilizes the joint with a splint or bulky bandage. However, the application of elastic wrap may produce a wide range of pressures on the injured limb. The incorrect pressure may retard venous or arterial circulation and may contribute to thromboembolism; pressure that is too high can induce tissue ischemia that further injures the tissue.

More complex pressure devices are available to patients suffering from various venous, circulatory and peripheral vascular diseases. These devices typically consist of an inflatable bladder in the form of a sleeve that can be placed around all or a portion of a patient's arm or leg. The bladder is connected to a pump that alternately inflates and deflates the bladder. In some such devices, the sleeve placed around the extremity includes a number of sequential bladders along the axial length of the sleeve to allow the sleeve to be inflated and deflated in a peristaltic manner along its length. By alternately inflating and deflating the bladder or bladders contained within the sleeve, circumferential pressure is applied to the patient's extremity, thus aiding in the circulation of blood there through. Such systems are currently used to treat venous insufficiency, prevent deep venous thrombus and control lymphedema and improve tissue perfusion in patients with peripheral arterial disease.

Other medical devices such as catheters and tracheotomy tubes are placed into a body lumen and then held in place with an inflatable balloon at the distal end of the device. The balloon is subject to over-inflation, however, again resulting in possible damage to treated tissue.

In addition, current systems tend to be expensive and complex, frequently being coupled to feedback circuits to control changes in pressure. Compression systems have been known to malfunction and cause undesirable variability in or increase in the applied pressure. Even when such systems are controlled by the patient, they may be subject to incorrect operation resulting in over-inflation of the sleeve. For such a system used to correct venous insufficiency in a limb, for example, incorrect operation is at best painful and at worst results in loss of the limb. Finally, most patients complain of some level of pain during inflation due to the rapid increase in pressure against the extremity.

In view of the above, the need exists for therapeutic devices that are capable of applying pressure but which are unable to produce over-pressure at the site of damage or disease. Such devices should be simple to use, allow peristaltic pumping at a variety of pressures, and have the ability to apply heat or cold.

SUMMARY OF THE INVENTION

The present invention relates to therapeutic devices that provide support or pressure to tissue. In particular, the invention relates to such devices comprising open cell foam useful in the treatment of diseases and injuries. The open cell foam is in a relaxed or relaxed state until application of vacuum resulting in an evacuated state. The foam is engineered to produce a device that has characteristics that provide a maximum desirable pressure and that will avoid the possibility of over-pressure which can result in tissue damage or necrosis.

In a first aspect, this invention is a medical device for applying pressure to tissue comprising a body portion having a relaxed state and a contracted state, the body portion being configured to apply pressure to tissue in the relaxed state, the body portion adapted to contain a fluid; and a fluid controller fluidly connected to the body portion for removing fluid contained in the body portion, the body portion being configured to contract from the relaxed state to the contracted state upon removal of fluid from the body portion. The body portion may comprise foam and preferably comprises open cell foam. The body portion also may include a fluid impermeable outer coating. The medical device may also comprise a fluid source and a valve, the valve being connected between the body portion and the fluid source and fluid controller, the valve having a first position for connecting the body portion to the fluid controller and a second position for connecting the body portion to the fluid source. The fluid controller may be a vacuum source. The valve preferably is programmable and the valve may be programmed to switch between the first position and the second position. The medical device may comprise a bladder fluidly connected to a liquid wherein the liquid is hot or cold.

In a second aspect, this invention is a medical device for applying pressure to a human or animal limb comprising a body portion having a substantially cylindrical shape sized to fit over the limb, the body portion being adapted to contain a fluid and further having a relaxed state and a contracted state, the body portion being configured to apply pressure to the limb in the relaxed state, and a fluid controller fluidly connected to the body portion for removing fluid contained in the body portion, the body portion being configured to contract from the relaxed state to the contracted state upon removal of fluid from the body portion. The body portion may comprise open cell foam and may include a fluid impermeable outer coating.

In a third aspect, this invention is a medical device for applying pressure to tissue comprising a body portion having at least two separate compartments, each compartment having a relaxed state and a contracted state and being configured to apply pressure to tissue in the relaxed state, the compartments being adapted to contain a fluid, and a fluid controller fluidly connected to each compartment of the body portion for removing fluid contained in the body portion, each compartment being configured to contract from a relaxed state to a contracted state upon removal of fluid from the compartment. The device may include valves, the valves being connected between each compartment and the fluid source and fluid controller and having a first position for connecting the compartment to the fluid controller and a second position for connecting the compartment to the fluid source. Each compartment may be separately cycled between the first and second position of the at least one valve in a sequence so as to apply pressure to tissue in a peristaltic manner.

In a fourth aspect, this invention is a medical device for applying pressure to tissue comprising a body portion having a first region configured to apply a first pressure to tissue and a second region configured to apply a second pressure to tissue, each region having a relaxed state and a contracted state and capable of applying pressure to tissue in the relaxed state, the regions being adapted to contain a fluid, a fluid controller fluidly connected to the body portion for removing fluid contained in the body portion, each region being configured to contract from a relaxed state to a contracted state upon removal of fluid from the compartment, wherein the first pressure is not equal to the second pressure. The pressure of the first and second regions may form a gradient.

In a fifth aspect, this invention is a method of applying pressure to tissue comprising supplying, adjacent to the tissue, a device having a body portion, the body portion having a fluid impermeable exterior and a fluid containing interior; applying vacuum to the interior of the body portion to remove the fluid such that the body portion is in a contracted state; and removing the vacuum to the interior of the body portion to allow fluid to enter the interior such that the body portion is caused to expand to a relaxed state, the body portion in the relaxed state applying pressure to the adjacent tissue. The pressure may be alternately applied and removed from the tissue.

In a sixth aspect, this invention is a method of supporting a patient's body in a bed or chair comprising supplying a patient supporting structure having a plurality of compartments, each compartment having a fluid impermeable outer portion and a fluid containing inner portion; applying a vacuum to the inner portion of a first compartment such that the first compartment is in a contracted state and pressure between a first portion of the patient's body and the outer portion of the first compartment is reduced; removing the vacuum from the inner portion of the first compartment such that the first compartment is caused to expand to a relaxed state such that increased pressure is applied to the first portion of the patient's body by the outer portion of the first compartment; applying a vacuum to the inner portion of a second compartment such that the second compartment is in a contracted state and pressure between a second portion of the patient's body and the outer portion of the second compartment is reduced; removing the vacuum from the inner portion of the second compartment such that the second compartment is caused to expand to a relaxed state such that increased pressure is applied to the second portion of the patient's body by the outer portion of the second compartment; and cycling between the applying steps and the removing steps in the first and second compartments so that the pressure applied to the first and second portion s of the patient's body is varied.

In a seventh aspect, this invention is a method of holding a medical device in place in a body lumen comprising providing a device having a support element in communication with a fluid line; the support element having a relaxed state at ambient pressure and a contracted state at reduced pressure; removing fluid from the support element to produce the contracted state; advancing the device through the lumen with the support element in the contracted state; positioning the device at a desired location within the body lumen; and admitting fluid at ambient pressure to the support element, thus returning the support element to the relaxed state, the support element in the relaxed state being configured to provide pressure against the body lumen to hold the medical device in place.

In an eighth aspect, this invention is a medical device comprising a body portion comprising a material adapted to contain a fluid, the material having a first size when filled with the fluid and a second smaller contracted size when the fluid is removed, the material being selected to be in a relaxed condition when filled with fluid and to resist contraction to the second size when fluid is removed; and a fluid controller fluidly connected to the body portion, the fluid controller being configured to remove fluid from the body portion.

The therapeutic device of this invention offers numerous advantages over devices currently in use. The maximum compressive force that can be applied to a patient's tissue is the force applied by the open cell foam in its relaxed state. By a proper selection of a foam with specific physical characteristics, it is possible to predetermine the amount of force to be applied to a patient's limb, and thereby prevent discomfort, pain and injury that can occur by providing excess pressures to a limb or body tissue. As such, the devices of this invention do not cause discomfort or injury to the patient due to malfunction or improper operation. In addition, the present invention provides a simple and inexpensive way of achieving a peristaltic action on the limb of a patient suffering from circulatory or a peripheral vascular disease.

DETAILED DESCRIPTION OF THE INVENTION

The devices of this invention comprise a body portion made of a material that is capable of being contracted from its relaxed or resting state to an evacuated or contracted state. "Relaxed state" refers to the condition of the material when no external forces are acting on it to cause the material to expand or contract. The evacuated or contracted state of the material is produced by removal of fluid contained within the material. The terms "evacuated" and "contracted" refer to the application of vacuum on the material resulting in a reduction of pressure within the material as compared to ambient pressure. Vacuum can be applied by means of various pumps, aspirators, and suction devices.

Any material that is capable of being contracted from a relaxed state to an evacuated state may be used in the devices of this invention. Preferably, the material is an engineered open cell foam. A piece of the open cell foam in a relaxed state is larger than the same piece in an evacuated state. In its relaxed state, the open cell foam is at ambient pressure; that is, the pressure inside the foam is that same as that outside the foam. The open cell foam is in a relaxed state until application of vacuum (for example, due to suction from a water aspirator or from a syringe), resulting in an evacuated state. The foam is designed to apply a desired pressure to the tissue of a patient in its relaxed state. One such suitable foam is commercially available from New Dimension Industries, Inc., of Moonachie, N.J., under the designation "2000 YELLOW".

Figure 1A:
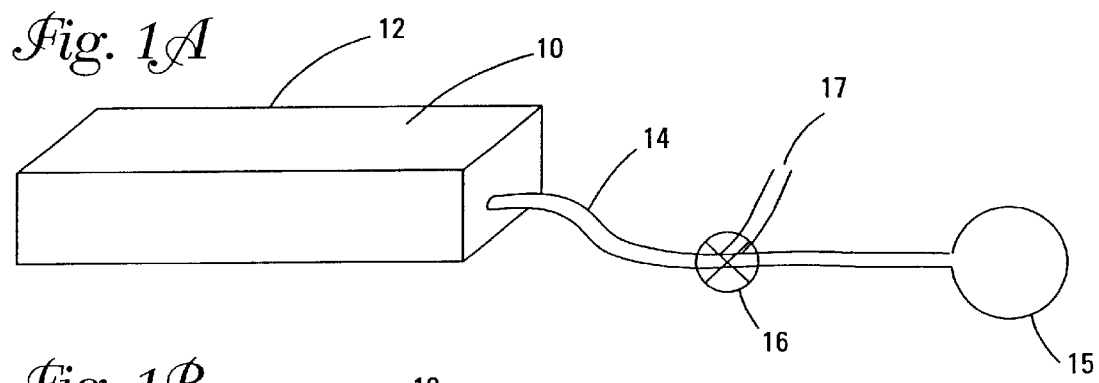
FIGS. 1A to 1E illustrate the expansion and evacuation cycles of devices of the present invention.
Figure 1B:
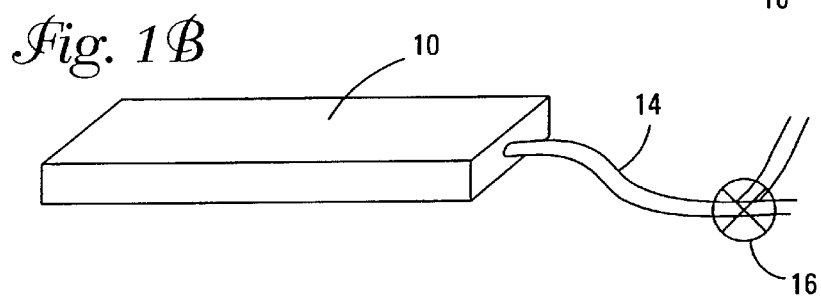
Figure 1C:
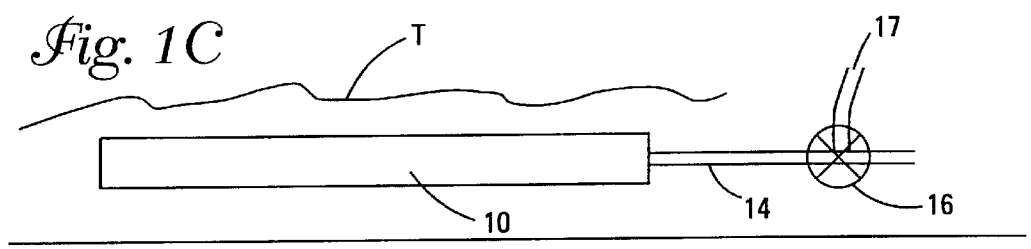
Figure 1D:
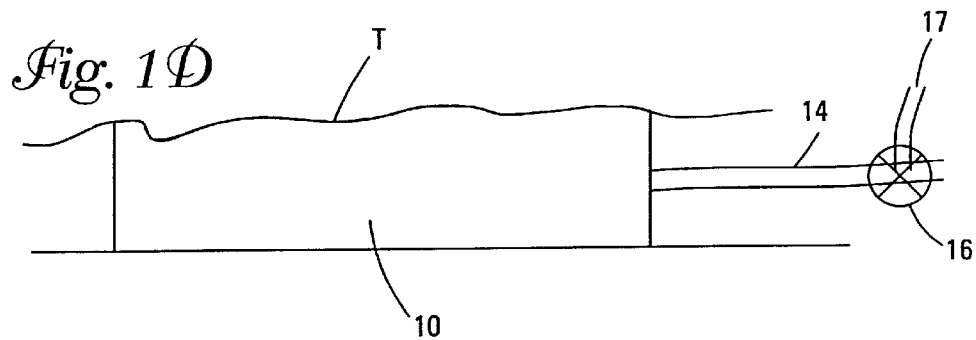
Figure 1E:
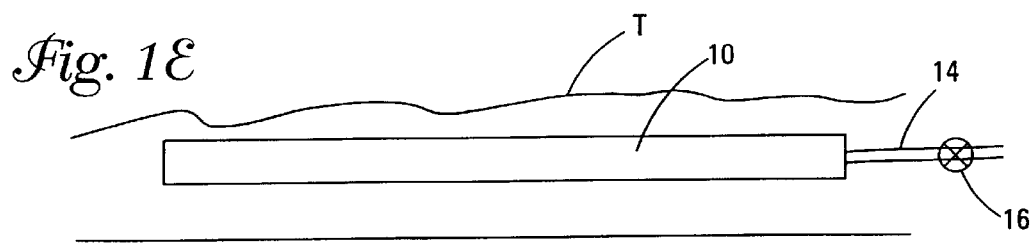

FIG. 1A illustrates the relaxed state of a material used for the medical devices of this invention. Foam 10 is covered with generally impermeable jacket or covering 12. This enables the body portion to assume and maintain a contracted, evacuated state when air is evacuated from the foam. Vacuum line 14 permits communication of air and vacuum with the foam. Vacuum line 14 is fitted with valve 16 which connects the foam to either vacuum source 15 or air/fluid source 17. Air/fluid source 17 may simply be open line 14 to the atmosphere or may be a line to a source of fluid, such as water. This may be a manual valve, such as a gate valve, controllable by a patient or physician, or it may be a solenoid valve that can be programmed to cycle the foam between the relaxed and evacuated states. FIG. 1B shows the valve open to vacuum resulting in evacuated state 10. FIG. 1C shows foam 10 positioned near tissue T that is to undergo treatment. FIG. 1D shows relaxed state foam 10 creating a pressure against the tissue. FIG. 1E shows the next step in the cycle, i.e., evacuation state of foam 10.

Devices of this invention use the ability of the foam to cycle between relaxed and evacuated states to treat circulatory disorders (e.g., venous insufficiency and peripheral arterial disease), to immobilize injured limbs, and to stabilize (i.e., hold in place) catheters, shunts, and the like to body lumens. For treatment of a limb, for example, a generally cylindrical device is fitted over the limb with the foam in the evacuated state. Air is admitted into the foam, resulting in an increase in size of the foam and application of pressure on the limb. For treatment of circulatory disorders, the foam cycles through the relaxed and evacuated state, thus stimulating venous flow of blood even in the absence of muscular action. Similarly, the foam can be used in devices wherein the foam is constrained to expand in one direction only, such as in an eye-patch. Devices comprising the foam may also be used in body lumens. The foam is an aid in positioning and holding in place, for example, catheters, intravenous tubing, and wire leads from electrodes by delivering and positioning the device with the foam in an evacuated state. The foam is returned to its relaxed state to apply a constant, desired pressure to the body lumen. The possibility of over-pressure, such as with conventional balloons, is avoided since the maximum pressure which is applied by the foam is a function of the material comprising the foam. The devices may also be used in blood vessels, during the positioning of a stent or shunt, and may be used to temporarily occlude the flow of blood. The foam in its relaxed state is engineered to have characteristics that provide a maximum desirable pressure to the tissue undergoing treatment. The devices are designed to avoid the possibility of over-pressure which can result in tissue damage or necrosis.

In a preferred embodiment, the foam comprises an open cell structure, although the foam may include some closed cells. The foam is capable of being reduced in size when air or other fluid is removed from the voids. This evacuated foam is capable of returning to its original size when air or other fluid is admitted into the foam. That is, admission of a fluid results in a restoration of the relaxed state of the foam. Vacuum is established by the application of vacuum in the foam by placing the foam in communication with a vacuum or suction source and preventing air or other fluid from entering the foam. This can be done by placing the foam within an impermeable, or air-tight, covering or coating. This vacuum source could be a vacuum pump or water aspiration. An empty syringe could also be used to produce sufficient vacuum, particularly for small devices.

Various open cell foams are known in the art and are described in, for example, Chapter 1 of "Low Density Cellular Plastics", ed. N. C. Hilyard and A. Cunningham, Chapman & Hall, 1994. Various sizes, shapes, and diameters of voids are present throughout an open cell foam. The open cell foam may also have some closed cells as artefacts of a manufacturing process or may be introduced as a way to control the characteristics of the foam. Such characteristics include the rate of return and the thickness increase from evacuated to relaxed state. In any event, fluid moves freely throughout the open cell foam, even in the presence of some closed cells. This is in contrast to a closed cell foam, in which the movement of fluid is not possible.

The foam used in the devices of this invention may have constant characteristics throughout the entire device, a gradient through the length of the device, or regions with different characteristics. That is, for example, in a sleeve positioned on a limb, it may be desirable to have the thickness, response time, percentage of closed voids, etc., vary along the length of the sleeve. Such variability in a sleeve can be useful in helping to provide pumping action to the blood in the limb.

Figure 2:
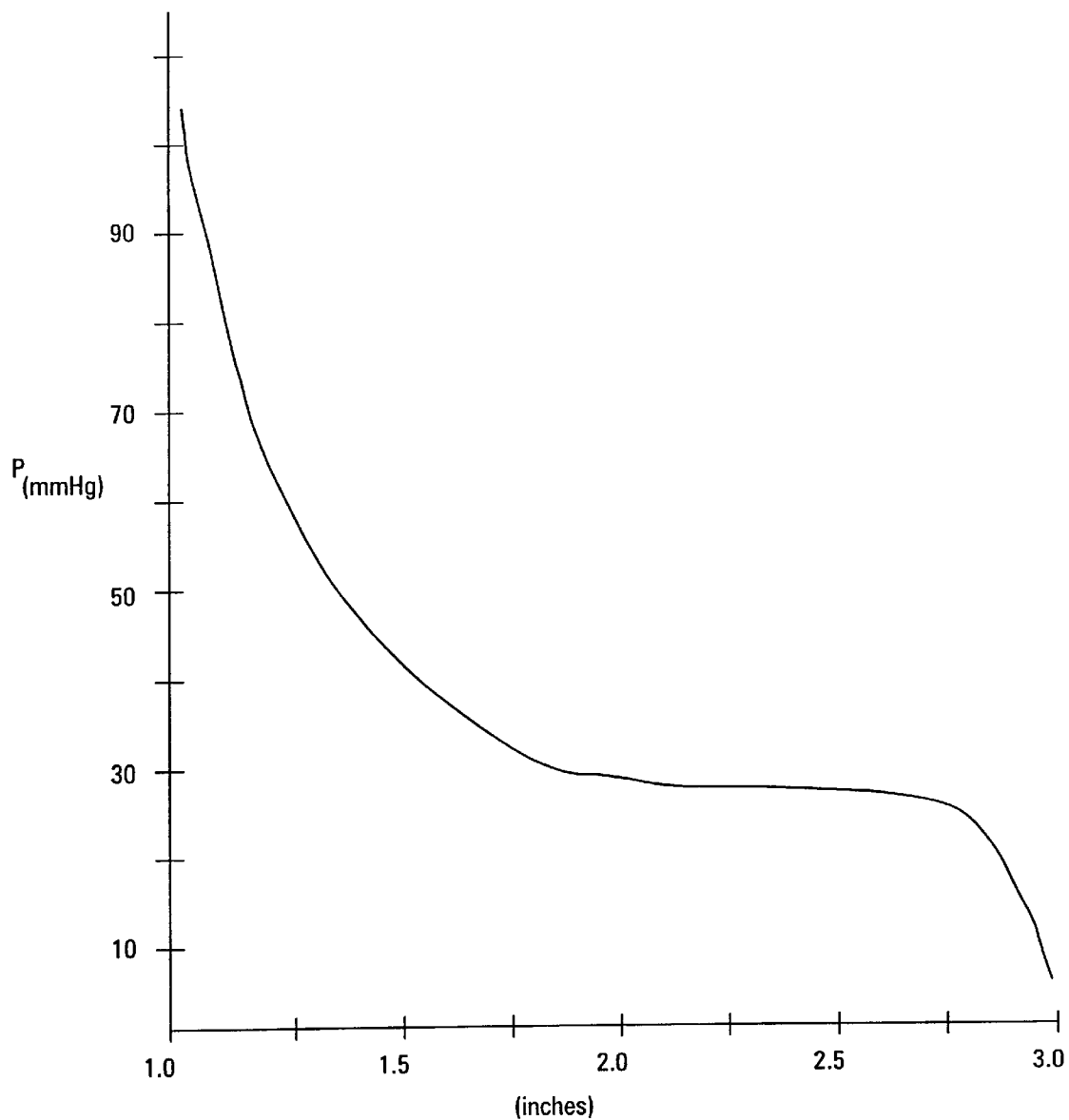
FIG. 2 is a thickness versus pressure graph of the open cell foam used in a preferred embodiment of this invention.

FIG. 2 is a graph illustrating how the pressure applied by an engineered open cell foam varies with the thickness of the foam. This graph was obtained by placing a 3 inch (7.6 cm) thick piece of open cell foam between two plates, compressing the foam, and measuring the force applied by the compressed foam against the plates. For use in this invention, it is desirable that the open cell foam have a region in the pressure/thickness curve wherein the pressure varies very little over a relatively large thickness change. That is, as shown in FIG. 2, for a 3 inch (7.6 cm) thick piece of foam compressed to thicknesses ranging between 2.0 and 2.75, the pressure ranges from about 28 to 24 mm Hg (3732.6 to 3199.4 Pa). This means that virtually the same pressure is being applied at these thicknesses when the foam is used in a device. The utility of this can best be exemplified by envisioning a device designed to fit a leg. A useful device must conform to the contour of the leg and yet should apply fairly constant pressure over the entire leg. Too much pressure can cause tissue damage and too little pressure is insufficient to support the leg. The device of this invention can be engineered to apply the same pressure to the entire leg simply by shaping the foam to follow approximately the contours of the leg.

A way of defining the desired relationship between pressure and thickness for devices of this invention is as follows. The open cell foam is compressed to different thicknesses, T1 and T2. When the absolute value of T1 minus T2 equals 0.5 inches (1.25 cm), the corresponding pressure difference preferably is less than 10 mm Hg (1333.1 Pa), more preferably less than 5 mm Hg (666.5 Pa), and most preferably less than 2 mm Hg (266.6 Pa). Where this region appears on the pressure vs. thickness graph will vary depending upon the characteristics of the foam and the thickness of the foam in its relaxed state. The important feature is that there is a region in the pressure vs. thickness curve that is relatively constant, i.e., near zero slope.

In the devices of this invention, the material (e.g., foam) is overlaid with an air-tight or impermeable covering or wrapping. The covering also may be adhered to the foam, for example, laminated or by means of adhesive. Suitable coverings are those that are both impermeable and sufficiently flexible to withstand many evacuation cycles without any cracking or damage; that is, preferably the covering remains impermeable and flexible during usage of the device. In addition, these coverings will be in contact with a patient's tissue and so must be biocompatible, non-irritating, and/or non-abrasive. For devices that lie against a patient's skin, the covering is selected based on comfort to the patient. In addition, the covering may undergo sterilization and should be compatible with sterilizing procedures. Typically the devices are sterilized by means of ethylene oxide (EtO) or by gamma radiation, as known to one of skill in the art.

Suitable impermeable coverings comprise polymeric fabrics and films, or cloth fabrics coated with a polymeric layer. One such suitable polymer coated fabric is a polytetrafluoroethylene (PTFE) coated nylon. PTFE also is referred to under the trade designation TEFLON™ fabrics and films. Silicone-impregnated fabrics, nylon fabrics, and rubberized fabrics are also suitable for use in the devices of this invention.

Figure 3:
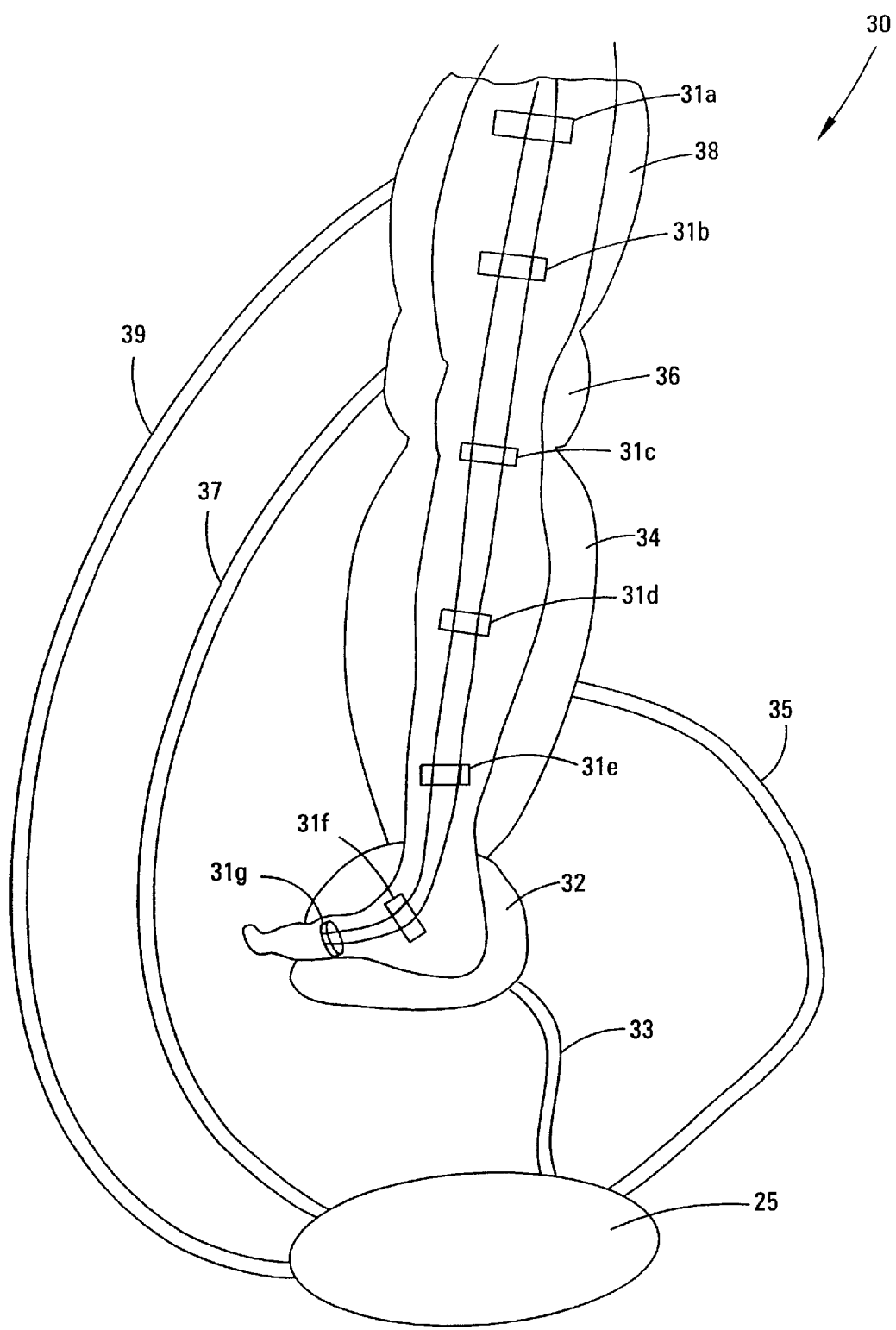
FIG. 3 is an illustration of a multi-pressure device on a patient's leg.

FIG. 3 illustrates another embodiment of the invention. This shows a device for the treatment of circulatory disorders (e.g., venous insufficiency) in a leg. It is to be understood that the device could be used on any limb or portion of limb that requires treatment. Device 30 is designed to treat vascular or lymphatic disorders and comprises an open cell foam in a generally cylindrical shape covered with an impermeable fabric. Inlets through the fabric permit fluid communication with the foam via vacuum/air lines. Device 30 has compartments 32, 34, 36 and 38 connected to air and vacuum lines 33, 35, 37, and 39, respectively. Device 30 is fastened on the leg by means of fasteners 31a to 31g. Lines 33, 35, 37 and 39 feed into fluid controller 25 which supplies vacuum and air by means of valves (not shown) to the compartments as desired. Preferably, the controller is programmed to vary the supply of air and vacuum by means of the valves so that the pressure is applied to the limb in the desired sequence. When fitted around a limb, device 30 forms a cylinder or sleeve having an axial passageway extending through it. The thickness of the cylinder walls range from about 1.5 to 3 inches (about 3.8 to 7.6 cm). The exterior diameter ranges from 6 to 10 inches (15.2 to 25.4 cm). The axial passage way additionally may be lined with a material which is comfortable against skin, such as polypropylene fabric. Other synthetic or natural fabric may be used. By varying the pressure of each compartment up the leg in sequence, the return flow of blood is stimulated. This is particularly useful after surgery or anytime that a patient is immobilized and venous flow is compromised.

The compartments comprise desired thicknesses of the open cell foam as described above, adapted to fit the desired portion of the leg and apply the desired pressure covered by an impermeable covering. The chambers each independently communicate with a vacuum pump. There is no communication between chambers. Thus, it is possible for one foam chamber to be evacuated while adjacent chambers are in their relaxed state. The compartments may be adjoined to each other or they may be separate. Typically such a device is provided as a cylindrical sleeve. The sleeve typically has a longitudinal slit along its length. The sleeve is placed around the patient's leg and then closures or fasteners are used to hold the sleeve in place. Such closures include straps comprising hook and loop tape. Alternatively, the closure may comprise an outer shell material such as a fabric sheet that is wrapped entirely around the sleeve and sealed using buttons, zippers, adhesives, hook and loop fasteners, and the like. Nylon fabric is a useful material for an outer shell. Regardless of the closure method selected, the closure must be sufficiently strong to allow the sleeve in its relaxed state to provide the desired pressure.

The device is placed on the leg (i.e., affixed with closures) with the open cell foam in its evacuated state. Air is then admitted to each compartment in turn, beginning with foot compartment 32. Vacuum is applied to foot compartment 32 as calf compartment 34 is allowed to fill with air. In this manner, blood is forced up the leg even in the absence of normal muscle activity. By selectively choosing which chambers are evacuated and which chambers fill with air, it is possible to alter the pressure along the leg. If the compartments are positioned along the longitudinal axis of the sleeve and subjected to suction forces in a sequential manner, peristaltic action occurs along the leg.

The device thus stimulates blood flow in the limb. The device is designed to cycle through many evacuation and filling cycles. Typically, treatments provide pressure to a limb for approximately 60 seconds followed a release of pressure lasting for times ranging from 30 to 60 seconds. The pressure applied depends on the clinical situation. For example, most patients need a pressure of 30 to 50 mm Hg (3999.24 Pa to 6665.4 Pa) for venous disease and deep vein thrombosis prevention, and a pressure of 60 to 80 mm Hg (7998.5 Pa to 10664.6 Pa) for lymphedema. Thus, the thickness of the open cell foam in the compartments, as well as the characteristics of the foam, are chosen to produce pressures and cycling times in the desired ranges.

Figure 4:
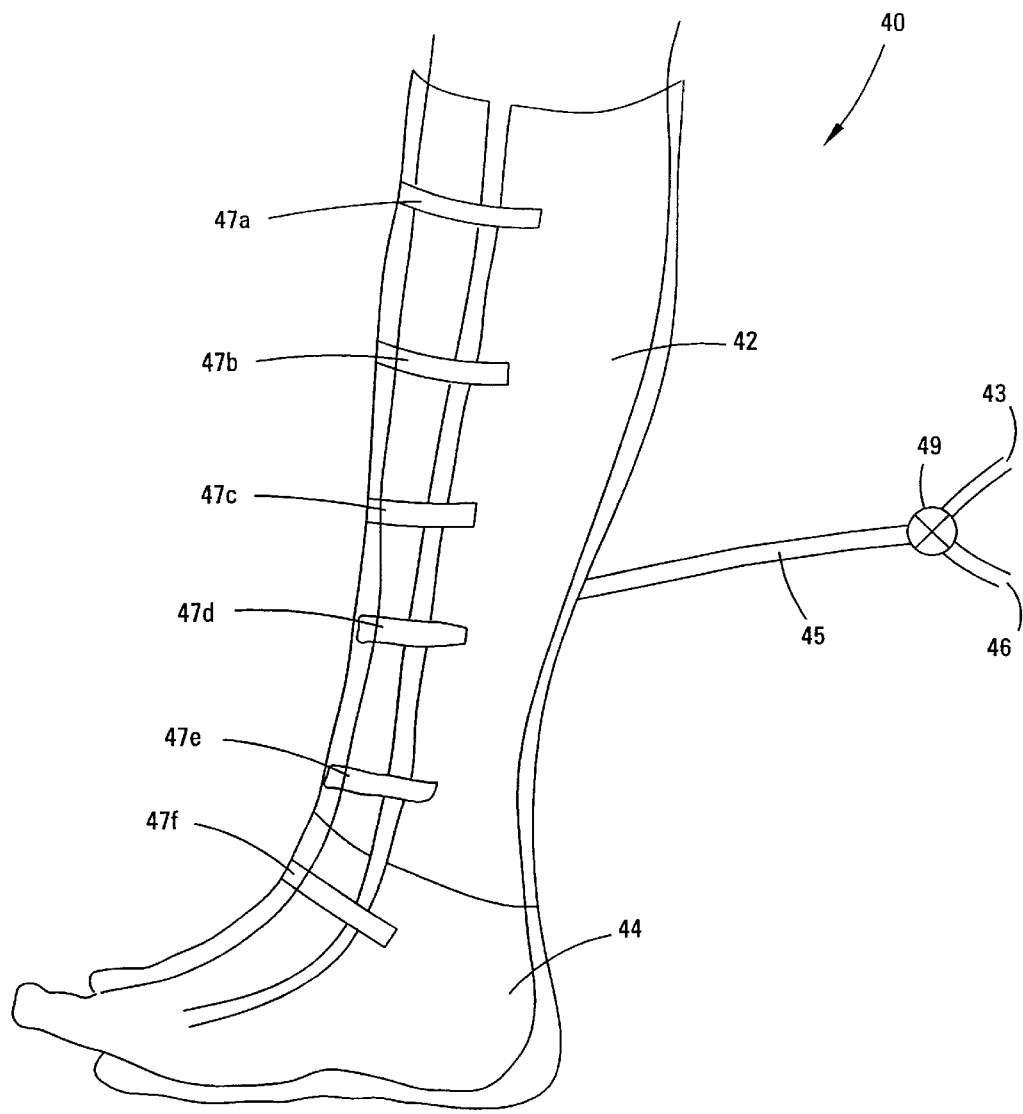
FIG. 4 is an illustration of a single pressure device on a patient's lower leg.

FIG. 4 illustrates a device for use in immobilizing a limb and/or for the treatment of circulatory disorders. Immobilization is particularly useful for treatment of acute injuries (e.g., sports injuries). Typically, for immobilization of a leg, the device would be one compartment, provided in a roughly cylindrical shape with a longitudinal slit down its length. The open cell foam is in fluid communication with vacuum and air lines to produce evacuated and relaxed states of the foam. The device would be placed on the limb of an injured person with the open cell foam in an evacuated state. Once air is admitted (e.g., by opening a valve), the foam would return to its relaxed state, thus applying pressure to the leg, controlling edema and also acting as a splint. Clearly, the pressure could be cycled with this device by alternately applying vacuum and admitting air. This invention provides the desired pressure to the leg, and is engineered so that it cannot exceed the desired pressure and cause further damage to the tissue.

Device 40 comprises calf chamber 42 and foot chamber 44. Foot chamber 44 articulates at the ankle. Chambers 42 and 44 are in communication with air and vacuum line 45, shown adjoining chamber 42. Line 45 is provided with valve 49, in communication with air and vacuum sources (not shown) via lines 43 and 46. Valve 49 can be turned manually, or may be a 20 microprocessor or controller which permits automatic flow of air and vacuum into the chambers. Device 40 is similar to device 30, described above, in that the thickness of the open cell foam varies depending upon the part of the leg. The compartments are covered by an impermeable covering. Device 40 forms a sleeve in use; a longitudinal slit along its length permits positioning of the sleeve on the calf and foot. Hook and loop fasteners 47a to 47f hold the sleeve in place. Other types of fasteners, such as snaps or zippers, could also be used.

Figure 5:
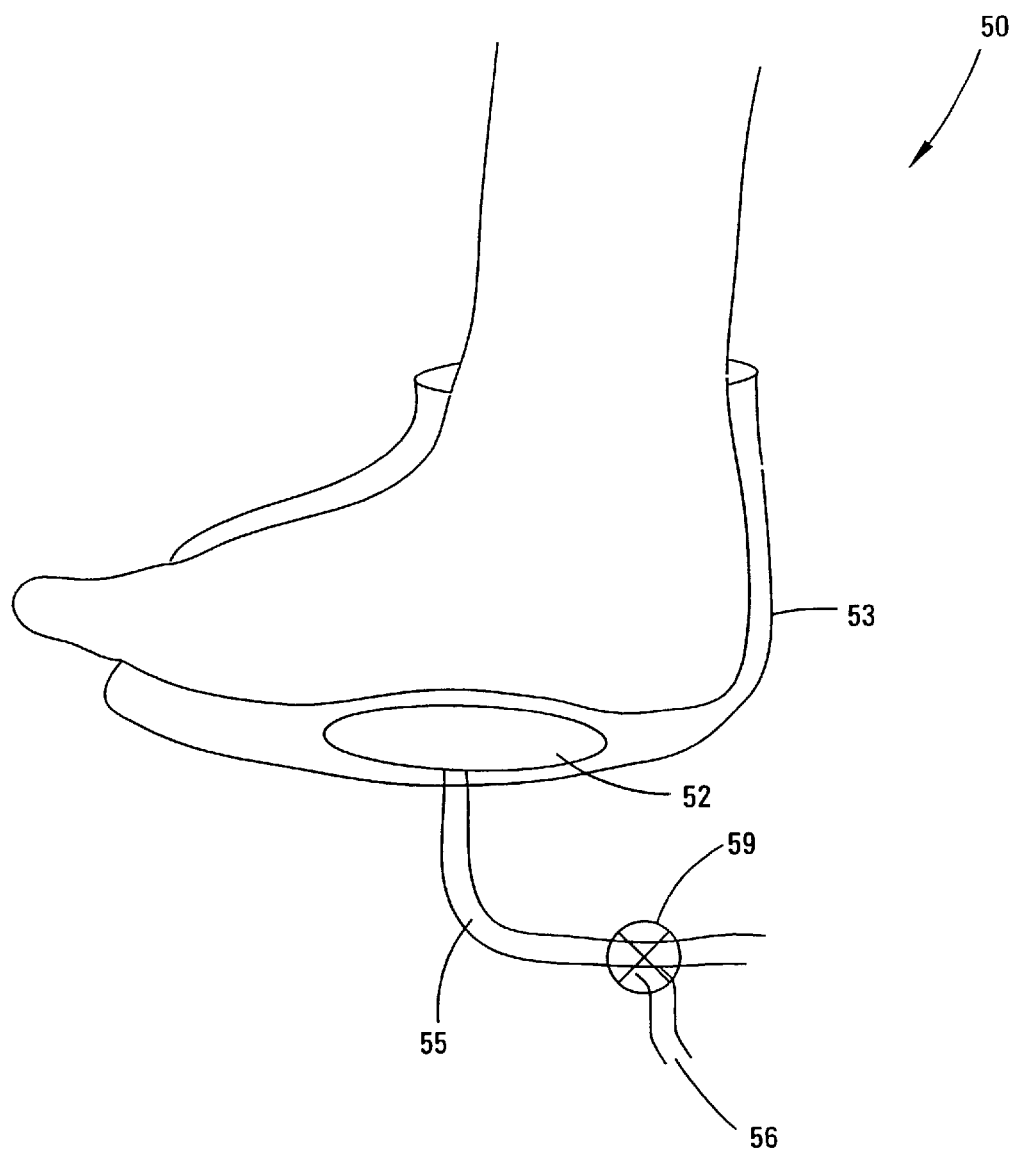
FIG. 5 is an illustration of a device on the plantar surface of the foot.

FIG. 5 illustrates a device that provides intermittent pressure to the bottom, or plantar area, of the foot. This device is used when a patient is unable to walk, as for example, after surgery, and helps prevent blood clots by causing blood to move up the leg. Device 50 comprises single compartment 52 in communication with air and vacuum sources (not shown) via line 55. Line 55 is provided with valve 59 that is turned to close off the source of air to line 55 and provide vacuum via line 56. Valve 59 may be manually operated or may be a microprocessor or the like. The open cell foam in the device is covered with impermeable covering 53. The thickness of the foam for such a device ranges from about 0.5 inch (1.2 cm) to about 2 inches (5.1 cm). The device is placed at the plantar arch in an evacuated state. The open cell foam is engineered to produce fast recoil and a pressure ranging from 80 to 100 mm Hg (10664.6 Pa to 13331 Pa). Typically, the device is in an evacuated state for 10 to 60 seconds and in its relaxed state for up to 5 seconds. This results in relatively brief bursts of pressure being applied to the plantar arch, resulting in the flow of blood up the calf.

Figure 6A:
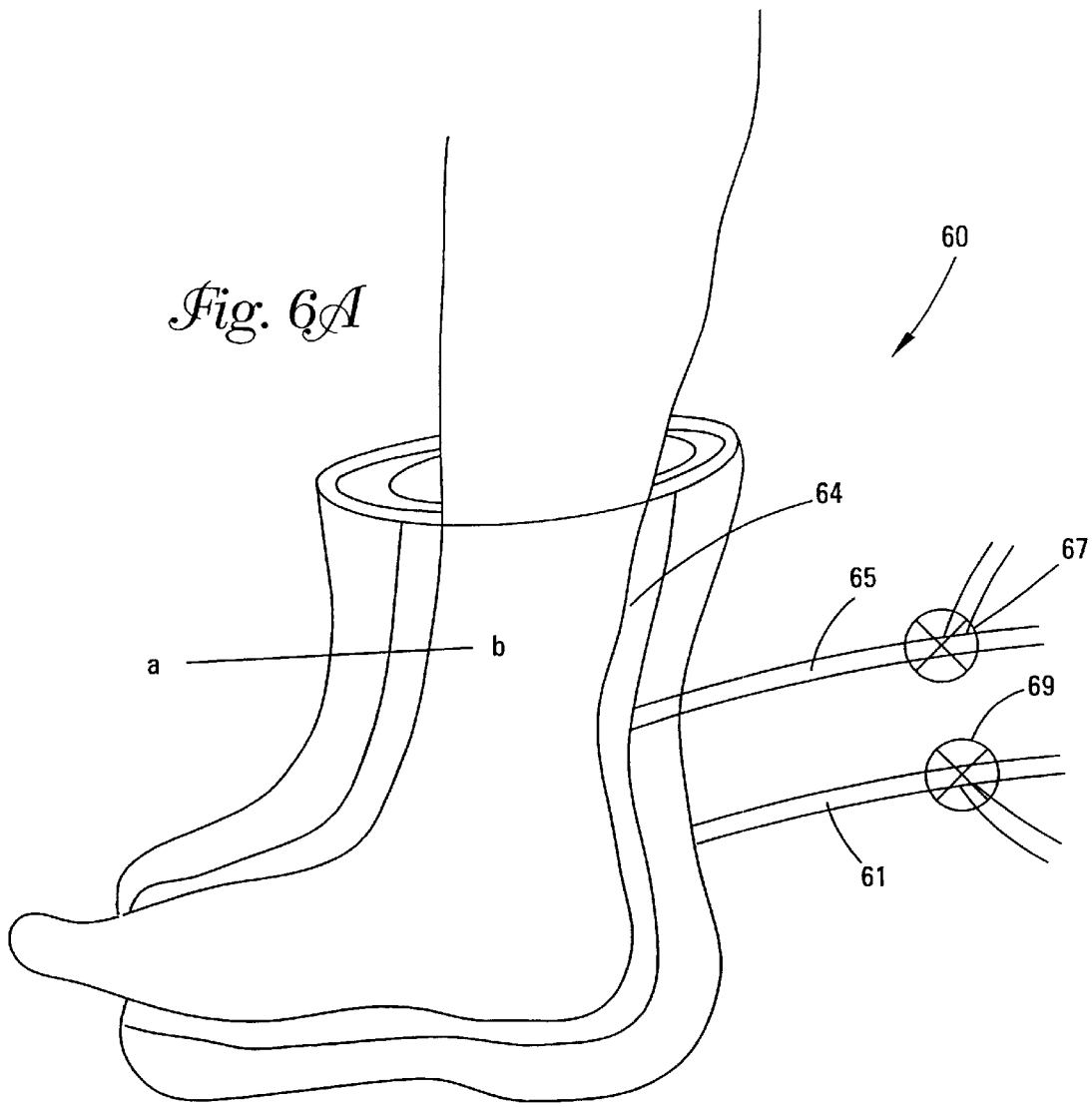
FIG. 6A is an illustration of an ankle injury device.
Figure 6B:
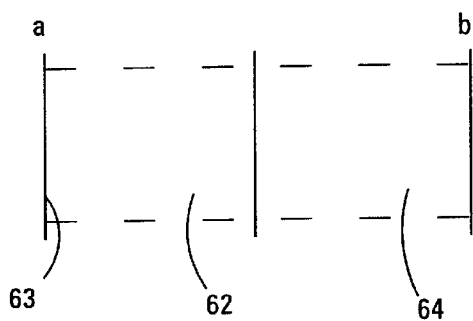
FIG. 6B is a cross-sectional view of a portion of the device of FIG. 6A.

FIG. 6A illustrates another device used for the treatment of acute injuries and shows such a device on an ankle. FIG. 6B shows a cross-section of the device along line a–b. Device 60 comprises open cell foam 62 covered with impermeable layer 63 which is fastened around the foot and calf and held in place with closures, similar to that described for the device in FIG. 3. This device permits treatment of an injured area with heat or cold by providing hot or cold liquid to bladder 64 via line 65. Valve 67 controls the admission of fluid to the bladder. FIG. 6A illustrates the bladder next to the skin of the patient but the bladder could form the outermost layer of the device. The device is wrapped around the ankle when the foam is in the evacuated state. The thickness of the foam is adjusted to adapt to the needed thickness for the foot, ankle, and calf. Air is admitted to the foam via line 61 to return the foam to its relaxed state and apply pressure to the area. A manual or microprocessor controlled valve 69 controls the admission of air and vacuum. The temperature of the liquid is selected depending upon the treatment desired. For example, for acute injury, it is frequently desirable to chill the area, to reduce swelling and tissue damage. Meanwhile, compression of the injury is also necessary to control edema. Device 60 is easily removed by unfastening the closures and applying a vacuum to produce the evacuated state of the foam. Thus, removal of the device does not cause more damage to the limb. Though FIG. 6A illustrates application of the device to an ankle, any body part suffering acute injury could be treated in this manner. In particular, injuries to the neck and to joints such as the knee, wrist, elbow, fingers, and toes benefit from treatment with a device illustrated in FIG. 6A. Treatment of an injured neck with such a device is particularly efficacious. For acute neck injuries, a patient typically is immediately immobilized with a neck brace and then transported to a hospital for further care. Conventionally used neck braces are difficult to remove and further make it difficult to perform other necessary treatment, such as a tracheotomy. Thus there is risk of further damage to a patient due to the manner of immobilization. The device of this invention may be easily loosened or removed once vacuum or suction (e.g., hospital suction) is applied.

Alternatively, rather than using a bladder or separate compartment to hold chilled fluid, a chilled liquid can be placed in communication with an inlet to the device when the foam is in its evacuated state. A valve opens and chilled fluid is drawn into the open cells of the foam. The sleeve becomes chilled by the presence of the chilled fluid, thereby serving to cool the body part contained within the sleeve. At the same time, the device is applying pressure to the body part, and, as shown in FIG. 6, immobilizing it. The liquid may be chilled by radiant cooling (i.e., refrigeration or immersion in ice water) or may be cooled as a result of an endothermic chemical reaction. Likewise, if it is desired to provide heat to the injured limb, a warm liquid can be provided, that liquid being heated radiant heating, an exothermic chemical reaction or by electromagnetic energy (i.e., microwave energy). It is expected that the foam will provide some insulating effect, thereby maintaining the fluid, and thereby the sleeve, at a temperature within a desired range for a period of time sufficient to provide an initial therapeutic effect.

Figure 7A:
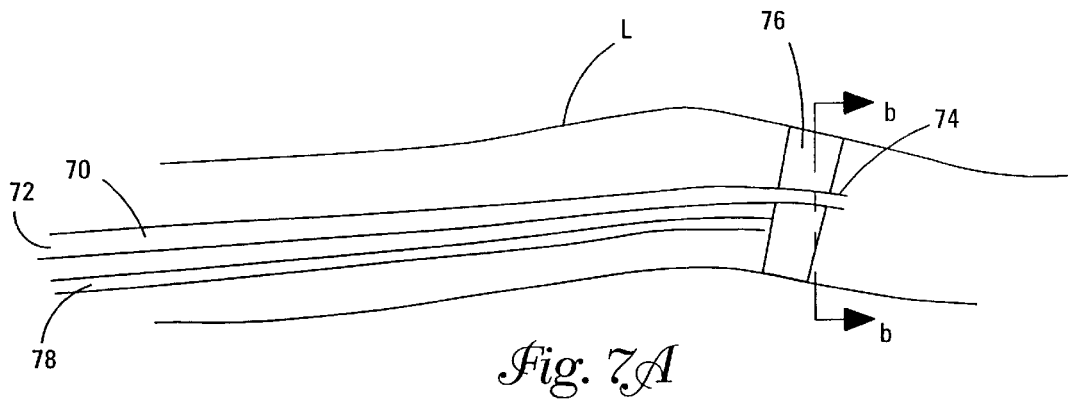
FIG. 7A is an illustration in longitudinal cross-section of a catheter.
Figure 7B:
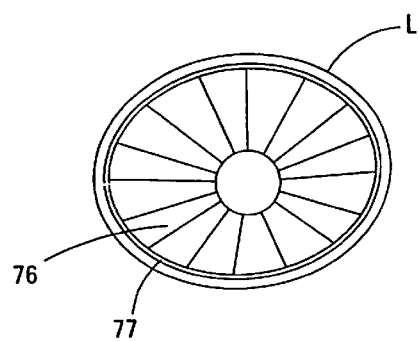
FIG. 7B is an illustration in transverse cross-section of the catheter of FIG. 7A.

FIGS. 7A and 7B illustrate the use of the open cell foam of this invention within a body lumen. A catheter in a body lumen is shown in longitudinal cross-section in FIG. 7A with a positioning device at the distal end of the catheter comprising the open cell foam and an impermeable covering. FIG. 7B shows the transverse cross-section of the catheter in the region of the foam. FIG. 7A shows a body lumen L, such as a blood vessel or a urethra, etc., having inserted in it catheter 70. Catheter 70 has a proximal end (that nearest the entry point of the device) 72 and a distal end 74. Near distal end 74 is open cell foam 76 disposed in an annular arrangement around distal end 74. An impermeable coating or covering 77 surrounds foam 76. The catheter is delivered with the foam in an evacuated state. The foam is in fluid communication via line 78 with a vacuum source (as, for example, a syringe; not shown) so that it may be returned to its evacuated state for removal of the catheter. Air or other fluid is admitted to the foam (either by separate communication with a source of fluid or through the catheter wall) and the foam expands to hold the catheter 70 in place.

Similarly, such a device could be used to position a shunt between two sections of blood vessel. The shunt would be delivered to the blood vessel with the foam in the evacuated state. Upon admission of air or other fluid, the foam returns to its relaxed state, thus pressing against the walls of the blood vessel and holding the shunt in place. The foam could also be used for vessel occlusion. Suction provided by syringe would be sufficient to remove air or other fluid from the foam and produce an evacuated state.

The devices of this invention can also be used in other body lumens, such as the esophagus, as an endotracheal tube. The advantage to such a device is that the pressure applied to the esophagus when the foam is permitted to return to its relaxed state would be unable to cause damage to tissue. That is, the foam would be engineered to provide the desired pressure for a range of diameters. Different sizes of tubes would, of course, be used depending upon the size of the patient's trachea (e.g., children as compared to adults). Current techniques of securing such tubes include using an inflatable balloon to hold the tube in place. These balloons need to be at a low pressure to prevent damage to the trachea. Properly engineered foam would provide sufficient pressure to place the tube with no danger of overinflation, such as occurs when using the balloons.

Figure 9:
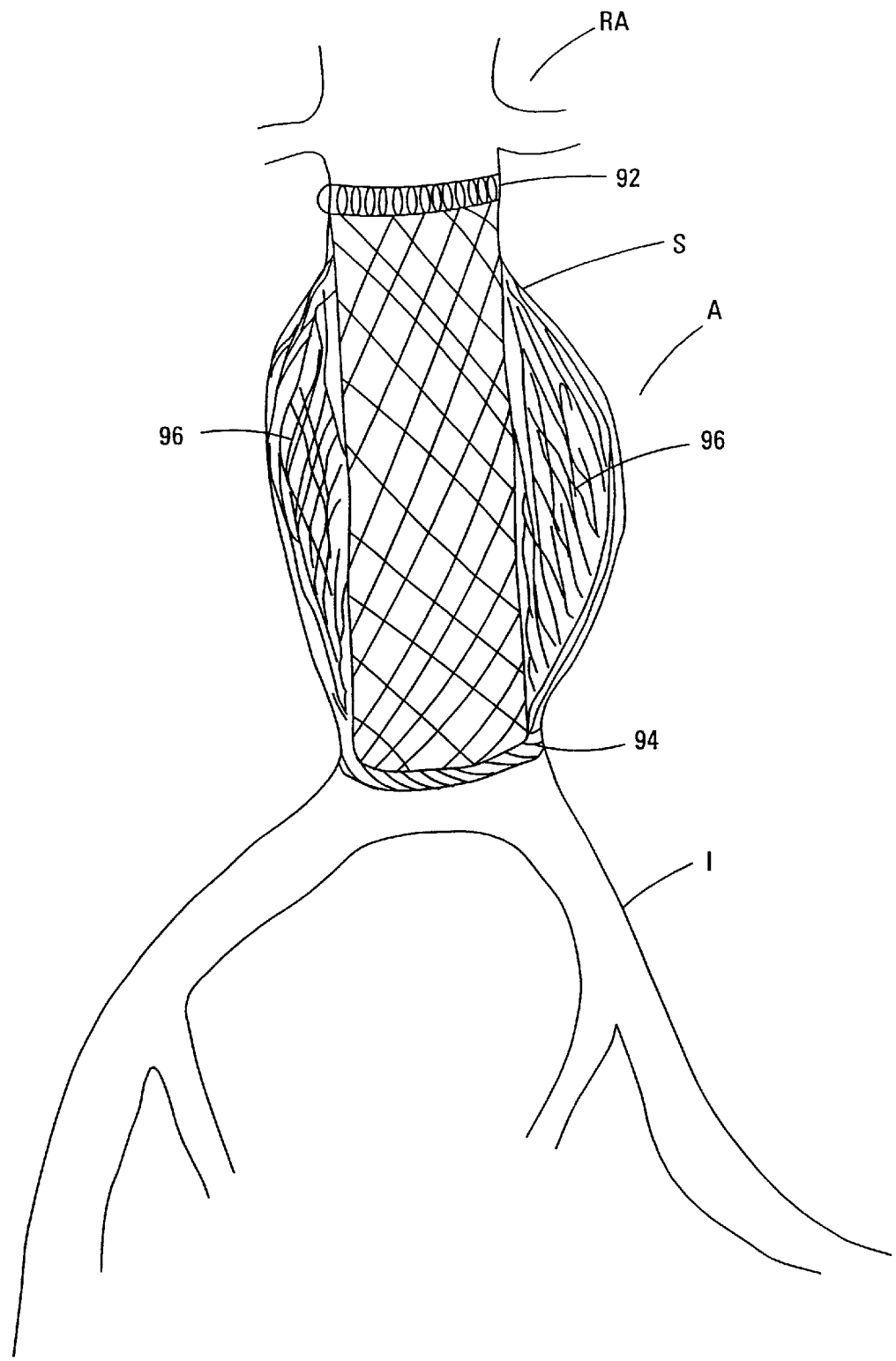
FIG. 9 is a diagrammatic view of a portion of a human vascular system depicting an abdominal aortic aneurysm in which a stent and foam device is deployed.

FIG. 9 illustrates the placement of a stent in abdominal aortic aneurysm A. The aneurysm begins below the renal arteries RA but does not extend into either of the common iliac arteries I. The stent spans the aneurysm and is seated at its cranial (i.e., near the head) portion 92 and caudal portion 94 by means of foam. Foam 96 also fills the region between the stent and the walls of the artery, providing support to the arterial walls. The foam preferably would be covered or coated with material that is biocompatible with the vasculature. The stent would be delivered to the aneurysm with the foam in an evacuated state. The foam would be engineered so that the pressure at the cranial and caudal ends of the stent would be sufficient to assist in holding the stent in place. The foam filling the space between the stent and the arterial walls likely would be engineered to apply less pressure than that engineered for either the cranial or caudal ends of the stent.

It is also contemplated that a foam device could be used to occlude or embolize a vessel; for example, a blood vessel having an aneursym, particularly in the brain. Current treatments of brain aneurysms include inserting a balloon into an aneurysm; potential problems with this include loss of pressure of the balloon, rendering it ineffective. A foam device could not deflate, and the foam would be engineered to provide the proper pressure to the vessel walls.

Foam support devices are contemplated to be useful in other body cavities, such as that which may be created during surgery, as, for example, during a mastectomy. Such devices fill the space created and may help prevent fibrous growth as well as excess drainage. Alternatively, a foam device could be engineered to function as a scaffold to support tissue growth into a body cavity.

Another use of the foam support device is in a penile implant. Current inflatable penile implants use two or three inflatable cylinders implanted into the corpora cavernosa of the penis. A reservoir containing a fluid (e.g., saline) and a pump are implanted into the scrotum and/or abdomen. Erection is accomplished by pumping saline into the cylinders from the reservoir. To return the penis to a flaccid state, pressure is applied manually to the penis while a valve is actuated allowing the fluid to be forced back into the reservoir.

The foam of this invention, encased in a fluid-tight sheath, could be used in place of the inflatable cylinders. The foam could utilize a reservoir for the fluid but a pump would not be needed. Actuating a valve would permit fluid (e.g., air) in the reservoir to flow and allow the foam to expand to a predetermined state. To return to the flaccid state, pressure would be applied manually to the penis while the valve is open, forcing fluid into the reservoir, then the valve would be closed.

Advantages to the use of an engineered foam for a penile implant include the inability to over-inflate the implant (which possibly results in rupture), the ability to use either a gaseous or liquid fluid to expand the foam, and reduction in system complexity by not requiring a pump.

Figure 8:
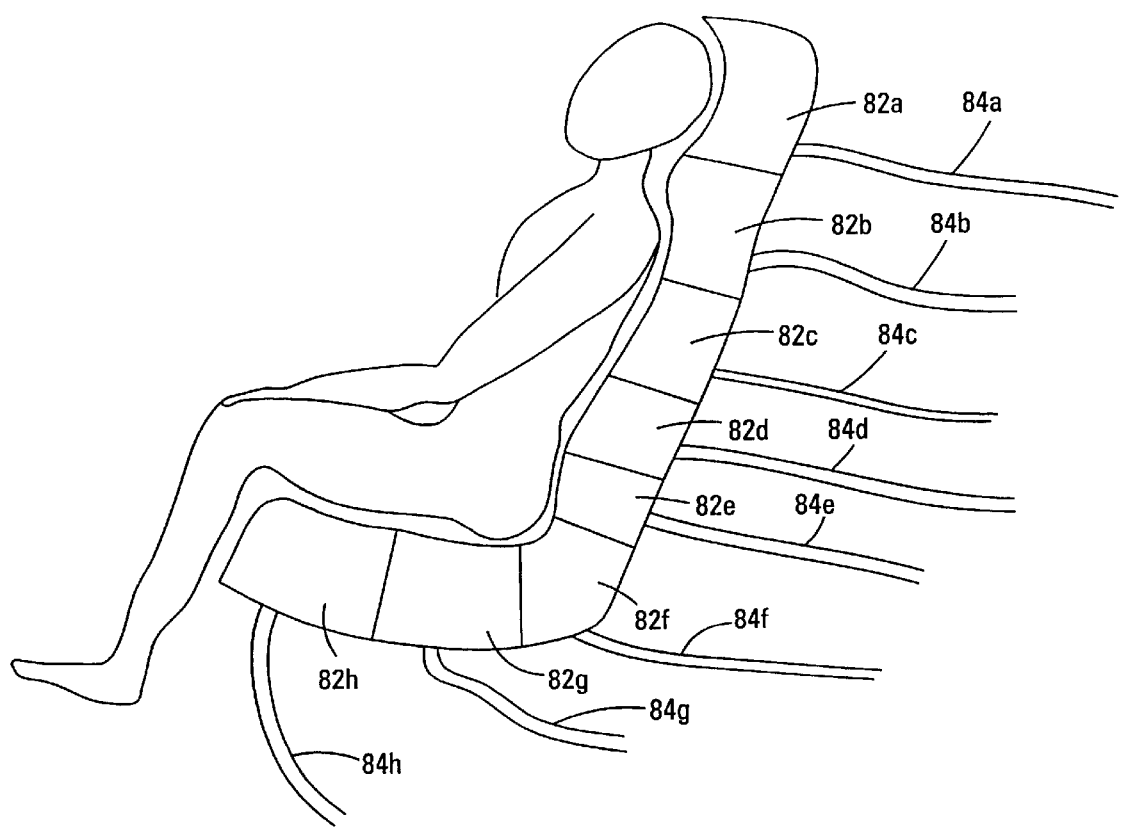
FIG. 8 is an illustration of a foam support device.

The foam of this invention is also contemplated for use in a support device, such as a bed or chair, as illustrated in FIG. 8. In this example, compartments 82a to 82g are in communication with air and vacuum via lines 84a to 84g. The admission of air and vacuum is controlled by valves 86a to 86g such as those described above. Preferably the variation of pressure provided by the support surface to the patient is varied automatically, such as controlled by a computer. This device prevents bed sores and pressure ulcers, such as happen when a patient cannot move for long periods of time. The use of open cell foam along with application of alternating vacuum and admission of air provides a device in which the pressure can be varied to prevent damage to tissue.

In each of the embodiments discussed above, it has been assumed that the material comprising the body portion automatically returns to its relaxed state upon release of an external force (e.g., vacuum). While this constitutes one preferred embodiment, it is to be understood that, that is not the only way by which the material may achieve its expanded, relaxed state. In particular, positive pressure could be provided to the material causing the material to expand to its predetermined relaxed state, or, in the embodiment in which a heated or chilled liquid is provided, the liquid may be provided under pressure to thereby return the material to its relaxed state. Regardless of the type of expansion force used, however, it is intended that the device be selected such that it provides a maximum, predetermined compression force to the patient's limb when the material is expanded. Unlike conventional compression systems that employ a bladder, it is intended that the relaxed state of the material places the material in its maximum volume configuration, thereby preventing over-inflation or over-pressure.

Although particular embodiments have been disclosed herein in detail, this has been done for purposes of illustration only, and is not intended to be limiting with respect to the scope of the claims. In particular, it is contemplated that various substitutions, alterations, and modifications may be made to the invention without departing from the spirit and scope of the invention as defined by the claims. For instance, the composition of materials is believed to be a matter of routine for a person of ordinary skill in the art with knowledge of the embodiments disclosed herein.

What is claimed is:

1. A medical device for applying pressure to tissue comprising:
    a body portion having an expanded position and a contracted position, the body portion being in a relaxed state when in the expanded position, the body portion being configured to apply a therapeutically effective amount of pressure to tissue in the relaxed state, the body portion adapted to contain a fluid; and
    a fluid controller fluidly connected to the body portion for removing fluid contained in the body portion, the body portion being configured to contract from the expanded position to the contracted position upon removal of fluid from the body portion.

2. The medical device of claim 1 wherein the body portion comprises foam.

3. The medical device of claim 2 wherein the body portion comprises open cell foam.

4. The medical device of claim 1 wherein the body portion includes a fluid impermeable outer coating.

5. The medical device of claim 1 further comprising a fluid source and a valve, the valve being connected between the body portion and the fluid source and fluid controller, the valve having a first position for connecting the body portion to the fluid controller and a second position for connecting the body portion to the fluid source.

6. The medical device of claim 1 wherein the fluid controller is a vacuum source.

7. The medical device of claim 5 wherein the valve is programmable.

8. The medical device of claim 7 wherein the valve is programmed to switch between the first position and the second position.

9. The medical device of claim 1 further comprising a bladder fluidly connected to a liquid wherein the liquid is hot or cold.

10. A medical device for applying pressure to a human or animal limb comprising:
    a body portion having a substantially cylindrical shape sized to fit over the limb, the body portion being adapted to contain a fluid and further having an expanded position and a contracted position, the body portion being in a relaxed state when in the expanded position, the body portion being configured to apply a therapeutically effective amount of pressure to the limb in the relaxed state, and a fluid controller fluidly connected to the body portion for removing fluid contained in the body portion, the body portion being configured to contract from the expanded position to the contracted position upon removal of fluid from the body portion.

11. The medical device of claim 10 wherein the body portion comprises open cell foam.

12. The medical device of claim 10 wherein the body portion includes a fluid impermeable outer coating.

13. The medical device of claim 10 further comprising a fluid source and a valve, the valve being connected between the body portion and the fluid source and fluid controller, the valve having a first position for connecting the body portion to the fluid controller and a second position for connecting the body portion to the fluid source.

14. The medical device of claim 13 further comprising a cooling member to cool the fluid in the fluid source.

15. The medical device of claim 13 further comprising a heating member to heat the fluid in the fluid source.

16. The medical device of claim 13 wherein the valve is programmable.

17. The medical device of claim 16 wherein the valve is programmed to switch between the first position and the second position.

18. A medical device for applying pressure to tissue comprising:

a body portion having at least two separate compartments, each compartment having an expanded position and a contracted position, each compartment being in a relaxed state when in the expanded position, and being configured to apply a therapeutically effective amount of pressure to tissue in the relaxed state, the compartments being adapted to contain a fluid, and a fluid controller fluidly connected to each compartment of the body portion for removing fluid contained in the body portion, each compartment being configured to contract from the expanded position to the contracted position upon removal of fluid from the compartment.

19. The medical device of claim 18 wherein the body portion comprises open cell foam.

20. The medical device of claim 18 wherein the body portion includes a fluid impermeable outer coating.

21. The medical device of claim 18 further comprising valves, the valves being connected between each compartment and the fluid source and fluid controller and having a first position for connecting the compartment to the fluid controller and a second position for connecting the compartment to the fluid source.

22. The medical device of claim 21 wherein the at least two valves are programmable.

23. The medical device of claim 22 wherein the at least two valves is programmed to switch between the first position and the second position.

24. The medical device of claim 21 wherein each compartment is separately cycled between the first and second position of the at least one valve in a sequence so as to apply pressure to tissue in a peristaltic manner.

25. A medical device for applying pressure to tissue comprising:

a body portion having a first region configured to apply a first pressure to tissue and a second region configured to apply a second pressure to tissue, each region having an expanded position and a contracted position, each of the first and second regions being in a relaxed state when in the expanded position, and being capable of applying a therapeutically effective amount of pressure to tissue in the relaxed state, the regions being adapted to contain a fluid, a fluid controller fluidly connected to the body portion for removing fluid contained in the body portion, each region being configured to contract from the expanded position to the contracted position upon removal of fluid from the compartment, wherein the first pressure is not equal to the second pressure.

26. The medical device of claim 22 wherein the pressure of the first and second regions forms a gradient.

27. A method of applying pressure to tissue comprising:

supplying, adjacent to the tissue, a device having a body portion, the body portion having a fluid impermeable exterior and a fluid containing interior;

applying vacuum to the interior of the body portion to remove the fluid such that the body portion is in a contracted state; and removing the vacuum to the interior of the body portion to allow fluid to enter the interior such that the body portion is caused to expand to a relaxed state, the body portion in the relaxed state applying a therapeutically effective amount of pressure to the adjacent tissue.

28. The method of claim 27 further comprising alternately applying and removing vacuum to the interior of the body portion such that pressure is alternately applied and removed from the tissue.

29. A method of supporting a patient's body in a bed or chair comprising:

supplying a patient supporting structure having a plurality of compartments, each compartment having a fluid impermeable outer portion and a fluid containing inner portion;

applying a vacuum to the inner portion of a first compartment such that the first compartment is in a contracted state and pressure between a first portion of the patient's body and the outer portion of the first compartment is reduced;

removing the vacuum from the inner portion of the first compartment such that the first compartment is caused to expand to a relaxed state such that increased pressure is applied to the first portion of the patient's body by the outer portion of the first compartment;

applying a vacuum to the inner portion of a second compartment such that the second compartment is in a contracted state and pressure between a second portion of the patient's body and the outer portion of the second compartment is reduced;

removing the vacuum from the inner portion of the second compartment such that the second compartment is caused to expand to a relaxed state such that increased pressure is applied to the second portion of the patient's body by the outer portion of the second compartment; and cycling between the applying steps and the removing steps in the first and second compartments so that the pressure applied to the first and second portions of the patient's body is varied.

30. A medical device for applying pressure to tissue comprising:

a body portion having a relaxed position and a contracted position, the body portion being configured to apply a therapeutically effective amount of pressure to tissue in the relaxed position, the body portion having an exterior surface and an interior portion adapted to contain a fluid; and a vacuum source connected to the interior portion of the body portion for removing fluid contained in the body portion, the body portion being configured to contract from the relaxed position to the contracted position upon removal of fluid from the body portion.

31. The medical device of claim 30 wherein the body portion comprises open cell foam.

32. The medical device of claim 1 wherein the body portion includes a fluid impermeable outer coating.

33. A medical device for applying pressure to a human or animal limb comprising:

a body portion having a substantially cylindrical shape sized to fit over the limb, the body portion being adapted to contain a fluid and further having a relaxed position and a contracted position, the body portion being configured to apply a therapeutically effective amount of pressure to tissue in the relaxed position, and a vacuum source connected to the interior portion of the body portion for removing fluid contained in the body portion, the body portion being configured to contract from the relaxed position to the contracted position upon removal of fluid from the body portion.

34. The medical device of claim 33 further comprising a fluid source and a valve, the valve being connected between the body portion and the fluid source and vacuum source, the valve having a first position for connecting the body portion to the vacuum source and a second position for connecting the body portion to the fluid source.

35. The medical device of claim 34 further comprising a cooling member to cool the fluid in the fluid source.

36. A medical device for applying pressure to tissue comprising:

a body portion having at least two separate compartments, each compartment having a relaxed position and a contracted position, the body portion being configured to apply a therapeutically effective amount of pressure to tissue in the relaxed position, the compartments being adapted to contain a fluid, and a vacuum source connected to the interior portion of the body portion for removing fluid contained in the body portion, the body portion being configured to contract from the relaxed position to the contracted position upon removal of fluid from the body portion.

37. A medical device for applying pressure to tissue comprising:

a body portion having a first region configured to apply a first pressure to tissue and a second region configured to apply a second pressure to tissue, each region having a relaxed position and a contracted position, the body portion being configured to apply a therapeutically effective amount of pressure to tissue in the relaxed position, the regions being adapted to contain a fluid; and a vacuum source connected to the interior portion of the body portion for removing fluid contained in the body portion, the body portion being configured to contract from the relaxed position to the contracted position upon removal of fluid from the compartment, wherein the first pressure is not equal to the second pressure.

38. The medical device of claim 37 wherein the pressure of the first and second regions forms a gradient.

* * * * *